United States Patent

Razvan et al.

[11] Patent Number: 5,312,941
[45] Date of Patent: May 17, 1994

[54] BASIC CALCIUM ALUMINUM HYDROXIDE DICARBOXYLATES, A PROCESS FOR THEIR PRODUCTION AND THEIR USE

[75] Inventors: Coriolan Razvan, Karlsfeld; Reinhard Beck, Munich; Alfred Kürzinger, Karlsfeld; Michael Rosenthal; Albert W. Pürzer, both of Munich, all of Fed. Rep. of Germany

[73] Assignee: Bärlocher GmbH, Fed. Rep. of Germany

[21] Appl. No.: 98,307

[22] PCT Filed: Feb. 21, 1992

[86] PCT No.: PCT/DE92/00143
§ 371 Date: Aug. 6, 1993
§ 102(e) Date: Aug. 6, 1993

[87] PCT Pub. No.: WO92/15545
PCT Pub. Date: Sep. 17, 1992

[30] Foreign Application Priority Data

Feb. 28, 1991 [DE] Fed. Rep. of Germany ....... 4106404

[51] Int. Cl.$^5$ .......................... C07F 5/06; C07F 3/04; C08K 5/04; C08K 5/09
[52] U.S. Cl. ........................................ 556/179; 546/2; 524/99; 524/399
[58] Field of Search .................. 556/179; 524/399, 99; 546/2

[56] References Cited

U.S. PATENT DOCUMENTS

| | | | |
|---|---|---|---|
| 3,959,093 | 5/1976 | Merkl | 556/179 X |
| 4,425,278 | 1/1984 | Wirth et al. | 556/179 |
| 4,590,233 | 5/1986 | Erwied et al. | 524/99 X |
| 4,910,246 | 3/1990 | Burba et al. | 524/399 |
| 4,963,608 | 10/1990 | Kunieda et al. | 524/399 X |
| 5,075,472 | 12/1991 | Misra et al. | 556/179 |
| 5,169,892 | 12/1992 | Kawashima et al. | 524/399 X |
| 5,241,094 | 8/1993 | Razvan et al. | 556/179 |

FOREIGN PATENT DOCUMENTS

92/11421 8/1991 PCT Int'l Appl. .

Primary Examiner—Paul F. Shaver
Attorney, Agent, or Firm—Scully, Scott, Murphy & Presser

[57] ABSTRACT

The invention describes basic calcium aluminum hydroxide dicarboxylates of the general formula $$Ca_xAl_2(OH)_{2(x+3-y)}A_y \cdot m\, H_2O$$

wherein
x means 2 to 12, $$\frac{2x+5}{2} > y > 0$$

m means 0 to 12, and
A means an aliphatic, aromatic or heteroaromatic dicarboxylic acid anion or combinations thereof,
with the proviso that y≠1, if x=2–8
and a process for their production.

The compounds according to the invention are particularly suited as stabilizers for halogen-containing thermoplastic resins, in particular PVC.

10 Claims, No Drawings

BASIC CALCIUM ALUMINUM HYDROXIDE DICARBOXYLATES, A PROCESS FOR THEIR PRODUCTION AND THEIR USE

The invention relates to basic calcium aluminum hydroxide dicarboxylates, a process for their production and their use as stabilizers for halogen-containing thermoplastic resins, in particular polyvinyl chloride.

Thermoplastic halogen-containing resins, in particular PVC, are instable to the influence of heat and light. A thermal decomposition occurs e.g. during processing of e.g. unstabilized PVC. This manifests itself in a discolouring of the shaped article and in the deterioration of the mechanical properties. In order to exclude this disadvantage, it is necessary to incorporate heat stabilizers into the resin composition. For this purpose, organic and/or inorganic compounds of the metals lead, barium, cadmium, calcium, tin and zinc are customarily added alone or in combinations. Moreover, other co-stabilizers such as epoxides, organic sulphur compounds, polyols and phosphites are still added.

Basic lead compounds are preferably used to stabilize PVC articles, such as pipes, plates, profiles and cable insulations. The most frequently used basic lead compounds are of the sulphate, phosphite or stearate type.

DE-PS 12 19 223 and DE-OS 24 19 379 teach that PVC cable insulations are to be preferably stabilized with 2-basic lead phthalate, since this compound imparts excellent electrical properties to the cable.

It is mentioned in EP-A- 0 313 113 that 4-basic lead fumarate is the most effective basic lead compound for stabilizing plasticized halogen-containing vinyl polymer compositions. According to EP-A- 0 319 086, 5-basic lead fumarate imparts a higher stability and a better degree of whiteness to shaped PVC articles than other known lead stabilizers.

The organic and/or inorganic compounds of the heavy metals lead, barium and cadmium are classified as toxic. For this reason, it has been attempted for a long time to replace them by non-toxic compounds. The stabilizers on the basis of combinations of calcium and zinc carboxylates which are considered to be non-toxic are insufficient in their effectiveness in most fields of application. Their disadvantages manifest themselves in an insufficient long-term stability and/or an unsatisfactory initial colour and colour retention. The combination of these metal soaps with effective co-stabilizers, which improve the initial colour and long-term stability, is consequently imperative. It is described in FR-A 2 403 362 to stabilize plasticized PVC for cable insulations with a mixture of calcium zinc fatty acids, sorbitol and a β-diketone. EP-A-0 256 872 describes the use of hydrotalcite and a β-diketone for stabilizing PVC resins. The use of alkali alumo silicates in connection with other co-stabilizers in PVC was also suggested (DE-A-31 13 442).

However, all non-toxic stabilization systems suggested so far have disadvantages as compared with heavy-metal-containing stabilizers. They mostly do not have the necessary long-term stability. A good initial colour and a sufficient colour retention can only be achieved by using large amounts of expensive "colour improver". The metal-containing co-stabilizers hydrotalcite and zeolite are disadvantageous in that they split off volatile components at the processing temperatures necessary for the processing of PVC, for instance, which leads to a bubble formation in the shaped part. Moreover, shaped parts stabilized with e.g. polyol and/or zeolite absorb water, which leads to considerable problems during the further processing.

DE-A- 40 02 988 (prior art within the purview of Section 3 II of the German Patent Act) describes basic calcium aluminum hydroxide dicarboxylates of the formula

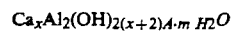
$Ca_xAl_2(OH)_{2(x+2)}A \cdot m\ H_2O$ wherein
x means 2 to 8,
m means 0 to 12, and
A means an aliphatic, aromatic or heteroaromatic dicarboxylic acid anion or combinations thereof,
a process for their production and their use as stabilizers for halogen-containing thermoplastic resins.

The invention is based on the object of providing new compounds and a process for their production, which are particularly suited as a stabilizer for halogen-containing polymers without having the aforementioned disadvantages of the known stabilizers, and are in particular considered as non-toxic.

This object is attained on the one hand by providing basic calcium aluminum hydroxide dicarboxylates of the general formula

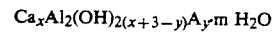
$Ca_xAl_2(OH)_{2(x+3-y)}A_y \cdot m\ H_2O$ wherein
x means 2 to 12, $$\frac{2x+5}{2} > y > 0$$

m means 0 to 12, and
A means an aliphatic, aromatic or heteroaromatic dicarboxylic acid anion or combinations thereof,
with the proviso that y≠1, if x=2–8.

In the aforementioned formula x means preferably 2 to 8, particularly preferred 3 to 6 and m means preferably 2 to 4.

The dicarboxylic acid anions indicated with A are e.g. derived from malonic acid, succinic acid, adipic acid, fumaric acid, maleic acid, phthalic acid, isophthalic acid, terephthalic acid and pyridine dicarboxylic acids. The fumarate and phthalate anion belong to the preferred dicarboxylic acid anions.

Examinations by means of x-ray diffraction showed that the dicarboxylates according to the invention do not belong to the hydrotalcite type as regards their crystal structure.

It became surprisingly apparent that the calcium aluminum hydroxide dicarboxylates according to the invention impart heat stabilities comparable to those of basic lead compounds to halogen-containing thermoplastic resins and the shaped parts produced therefrom. The initial colours and the colour retention of e.g. rigid PVC shaped parts stabilized with one of the new compounds according to the invention are equivalent to the same shaped parts containing known, non-toxic stabilizer systems.

On the other hand, the object on which the invention is based is attained by a process for the production of the calcium aluminum hydroxide dicarboxylates according to the invention, which is characterized in that mixtures of calcium hydroxide and/or oxide, aluminum hydroxide and sodium hydroxide or of calcium hydroxide and/or oxide and sodium aluminate are reacted with the corresponding dicarboxylic acid in amounts corresponding to the production of the desired compounds in an aqueous medium, and the reaction product is separated and recovered in a known fashion. The reaction product directly obtained from the aforementioned reaction can be separated from the aqueous reaction medium according to known processes, preferably by means of filtration. The processing of the separated reaction product is also carried out in a manner known per se, e.g. by means of washing of the filter cake with water and drying of the washed residue at temperatures of e.g. 60° to 130° C., preferably of 90° to 120° C.

Both a finely divided, active aluminum hydroxide in combination with sodium hydroxide and a sodium aluminate can be used for the reaction. Calcium can be used in the form of finely divided calcium oxide or hydroxide or mixtures thereof.

The reaction temperatures range preferably from about 25° to 100° C., more preferred between about 40° and 85° C. Catalysts or accelerators are not required, but can possibly also be used. The water of crystallization can be removed wholly or partly from the compounds according to the invention by means of thermal treatment.

When used as stabilizers, the dried calcium aluminum hydroxide dicarboxylates according to the invention do not split off any water at the processing temperatures of 160° to 200° C. e.g. customary for rigid PVC so that no disturbing bubble formation occurs in the shaped parts.

The compounds according to the invention can be coated in known fashion with surfactants to improve their dispersive power in halogen-containing thermoplastic resins.

According to the invention halogen-containing thermoplastic resins can be stabilized with the calcium aluminum hydroxide carboxylates according to the invention. Polyvinyl chlorides, homo- and copolymers thereof and their mixtures with other polymers such as ABS (copolymer of acrylonitrile/butadiene/styrene), CPVC (postchlorinated PVC), acrylates and the like, which are produced in known fashion, are particularly suited for this.

In addition to the compounds according to the invention, further additives can of course be incorporated into the resin. Examples of such additives are organotin compounds, organic phosphites, epoxy compounds, amino compounds, polyhydric alcohols, metal soaps of $C_8$-$C_{22}$ fatty acids with the metals Ca, Zn, Mg or Al, antioxidants, UV absorbers, carbonyl compounds, antistatic agents, lubricants, plasticizers, pigments and fillers.

The invention is explained in greater details by means of the following examples.

A) Production of the Basic Calcium Aluminum Hydroxide Dicarboxylates According to the Invention Example 1

An aqueous suspension (5.0 l) of 222 g of calcium hydroxide (3 mole) and 164 g of sodium aluminate (2 mole) is heated to 50° C. Subsequently 174 g of fumaric acid (1.5 mole) are added in the form of a 10% aqueous solution heated to 85° C. with stirring at a uniform feed speed in the course of 30 minutes. Thereupon the suspension is heated to 70° C. and stirred at this temperature for 2 hours. 10 minutes before the end of the reaction time, 4 g of sodium stearate are added for coating. The suspension obtained in this fashion is filtered off and washed with 1.8 l of water. The filter cake formed in this fashion is dried in a drying cupboard at 125° C. for 4 hours.

The analysis values of the product are indicated below.

|   | Mole ratio | |
|---|---|---|
|   | Found value | Calculated value |
| Ca | 3.0 | 3.0 |
| Al | 1.9 | 2.0 |
| C | 2.2 | 2.0 |

Example 2

An aqueous suspension (7.2 l) of 444 g of calcium hydroxide (6 mole), 80 g of sodium hydroxide (2 mole) and 156 g of active aluminum hydroxide (2 mole) is heated to 70° C. Subsequently, 498 g of phthalic acid (3 mole) in the form of a 8% aqueous solution (temperature 85° C.) are added with stirring at a uniform feed speed in the course of 30 minutes. Thereupon the suspension is heated to 80° C. and stirred at this temperature for 2 hours. 10 minutes before the end of the reaction time, 4 g of sodium stearate are added for coating. The suspension obtained in this fashion is filtered off, washed with 2.3 l of water, and the filter cake is dried in a drying cupboard at 130° C. for 4 hours. The analysis values of the product produced in this fashion are indicated below.

|   | Mole ratio | |
|---|---|---|
|   | Found value | Calculated value |
| Ca | 6.0 | 6.0 |
| Al | 2.1 | 2.0 |
| C | 16.4 | 16.0 |

B) Use of the Compounds According to the Invention as Stabilizers

The heat stability and the initial colour of shaped PVC bodies to which the compounds of the invention had been added are evaluated in the following examples.

For the evaluation of the heat stability the mixtures used in the following examples are homogenized and plastified in a laboratory rolling mill at 180° for 5 minutes. Square sample sheets with an edge length of 15 mm are cut from the about 1 mm thick milled sheet produced in this fashion. These sample sheets are tempered in a drying oven at 190° C. At 10-minute intervals one sheet each is removed and affixed to a test card one after the other. This procedure is repeated until the sample sheets turned black.

Example 3

|   | Parts by weight | | |
|---|---|---|---|
|   | A | B | C |
| PVC (K 68) | 100 | 100 | 100 |
| Chalk | 6 | 6 | 6 |
| TiO$_2$ | 3 | 3 | 3 |
| Stearyl stearate | 0.5 | 0.5 | 0.5 |
| Bisphenol A | 0.1 | 0.1 | 0.1 |
| Lead stearate | 1.0 | — | — |
| Dibasic lead phthalate | 2.0 | — | — |
| Calcium stearate | 0.5 | 0.8 | 0.8 |
| Zinc laurate | — | 0.8 | 0.8 |
| Ca$_3$Al$_2$(OH)$_{11}$(C$_4$H$_2$O$_4$)$_{0.5}$ | — | 3.0 | — |

-continued

|  | Parts by weight | | |
|---|---|---|---|
|  | A | B | C |
| $Ca_6Al_2(OH)_{14}(C_8H_4O_4)_{2.0}$ | — | — | 3.0 |
| Calcium acetyl acetonate | — | 0.1 | 0.1 |

The aforementioned compositions of A to C were tested according to the indicated method. The results are summarized in table I.

TABLE I

Results of the evaluation of the thermal stability

| Composition | Time (min.) | | | | | | | | | | |
|---|---|---|---|---|---|---|---|---|---|---|---|
|  | 0 | 10 | 20 | 30 | 40 | 60 | 80 | 100 | 120 | 140 | 160 |
| A | 1 | 1 | 1 | 1 | 3 | 3 | 3 | 3 | 3 | 5 | 5 |
| B | 1 | 1 | 1 | 1 | 2 | 2 | 2 | 4 | 4 | 4 | 6 |
| C | 1 | 1 | 1 | 2 | 2 | 2 | 2 | 4 | 4 | 4 | 6 |

1 = white
2 = slightly yellow
3 = slightly grey
4 = yellow
5 = grey
6 = brown

Example 4

|  | Parts by weight | | |
|---|---|---|---|
|  | D | E | F |
| PVC K 70 | 100 | 100 | 100 |
| Chalk | 40 | 40 | 40 |
| $TiO_2$ | 2 | 2 | 2 |
| Diisodecyl phthalate | 50 | 50 | 50 |
| Bisphenol A | 0.3 | 0.3 | 0.3 |
| Pentaerithritol | 0.1 | 0.1 | 0.1 |
| 2-basic lead phthalate | 2.0 | — | — |
| Lead stearate | 1.0 | — | — |
| Calcium stearate | 0.5 | 0.8 | 0.8 |
| Zinc laurate | — | 0.8 | 0.8 |
| $Ca_3Al_2(OH)_{11}(C_4H_2O_4)_{0.5}$ | — | 3.0 | — |
| $Ca_6Al_2(OH)_{14}(C_8H_4O_4)_{2.0}$ | — | — | 3.0 |

The aforementioned compositions of D to F were tested according to the indicated method, and the thermal stability was assessed. The results are summarized in table II.

TABLE II

| Composition | Time (min.) | | | | | | | | | |
|---|---|---|---|---|---|---|---|---|---|---|
|  | 0 | 10 | 20 | 40 | 60 | 80 | 120 | 160 | 180 | 200 |
| D | 1 | 1 | 1 | 1 | 1 | 3 | 3 | 3 | 3 | 5 |
| E | 1 | 1 | 1 | 1 | 1 | 2 | 2 | 4 | 4 | 6 |

TABLE II-continued

| Composition | Time (min.) | | | | | | | | | |
|---|---|---|---|---|---|---|---|---|---|---|
|  | 0 | 10 | 20 | 40 | 60 | 80 | 120 | 160 | 180 | 200 |
| F | 1 | 1 | 1 | 1 | 2 | 2 | 2 | 4 | 4 | 6 |

1 = white
2 = slightly yellow
3 = slightly grey
4 = yellow
5 = grey
6 = brown

We claim:

1. A basic calcium aluminum hydroxide dicarboxylate compound represented by the general formula $$Ca_xAl_2(OH)_{2(x+3-y)}A_y \cdot m\, H_2O$$

wherein
X is 2 to 12;

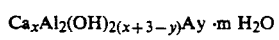

with the proviso that $y \neq 1$ if $x = 2$ to 8;
m is 0 to 12; and
A is an aliphatic, aromatic or heteroaromatic dicarboxylic acid anion or combination thereof.

2. The compound according to claim 1, wherein x is 2 to 8.

3. The compound according to claim 1, wherein x is 3 to 6.

4. The compound according to claim 1, wherein m is 2 to 4.

5. The compound according to claim 1, wherein A is a fumarate anion.

6. The compound according to claim 1 wherein A is a phthalate anion.

7. A process for the production of the compound according to claim 1 characterized in that mixtures of calcium hydroxide and/or oxide, aluminum hydroxide and sodium hydroxide or of calcium hydroxide and/or oxide and sodium aluminate is reacted with the corresponding dicarboxylic acid in amounts corresponding to the production of the desired compounds in an aqueous medium, and the reaction product is separated and recovered in a manner known per se.

8. A process according to claim 7, characterized in that the reaction is carried out at a temperature between about 25° and 100° C.

9. A process for stabilizing resins comprising adding a stabilizing effective amount of the compound of claim 1 to a halogen-containing thermoplastic resin.

10. The process according to claim 9 wherein the halogen-containing thermoplastic resin is polyvinyl chloride.

* * * * *

UNITED STATES PATENT AND TRADEMARK OFFICE
CERTIFICATE OF CORRECTION

PATENT NO. : 5,312,941
DATED : May 17, 1994
INVENTOR(S) : Coriolan Razvan, et al.

It is certified that error appears in the above-indentified patent and that said Letters Patent is hereby corrected as shown below:

On the Title Page, Section [30]: "4106404" should read --4106404 --

Column 2, line 8: "$Ca_xAl_2(OH)_{2(x+2)}A \cdot m\ H_2O$" should read -- $Ca_xAl_2(OH)_{2(x+2)}A \cdot m\ H_2O$ --

Signed and Sealed this

Twenty-fourth Day of January, 1995

*Attest:*

BRUCE LEHMAN

*Attesting Officer*      *Commissioner of Patents and Trademarks*